United States Patent [19]
Brainard et al.

[11] 4,002,175
[45] Jan. 11, 1977

[54] METHOD AND APPARATUS FOR CORTICAL THERMAL THERAPY

[75] Inventors: David M. Brainard; Edward C. Brainard, II, both of Marion, Mass.

[73] Assignee: Environmental Devices Corporation, Marion, Mass.

[22] Filed: June 25, 1975

[21] Appl. No.: 590,099

[52] U.S. Cl. .............................. 128/399; 128/380
[51] Int. Cl.² .......................................... A61F 7/00
[58] Field of Search .......... 128/399, 400, 401, 402, 128/380, 254

[56] References Cited
UNITED STATES PATENTS

| | | | |
|---|---|---|---|
| 2,429,583 | 10/1947 | Ogle | 128/380 X |
| 2,718,584 | 9/1955 | Hariu | 128/380 |
| 3,074,410 | 1/1963 | Foster | 128/400 |
| 3,897,790 | 8/1975 | Magilton et al. | 128/400 |

OTHER PUBLICATIONS

J. H. Magilton et al., The Physiologist, vol. 10, No. 3, Aug. 1967, p. 241.

*Primary Examiner*—Lawrence W. Trapp
*Attorney, Agent, or Firm*—Kenway & Jenney

[57] ABSTRACT

A method and apparatus for enhancing a person's cerebral functions by providing a selective increase in the cerebral temperature while leaving the temperature of the rest of the body as is. The method and apparatus elevate the exterior skull temperature to a selected value within the range between 38° and 50° Celsius and change the temperature within a limited rate.

9 Claims, 7 Drawing Figures

METHOD AND APPARATUS FOR CORTICAL THERMAL THERAPY

BACKGROUND OF INVENTION

This invention relates to the enhancement of human cerebral functions without resort to surgery or to chemicals. More particularly the invention provides a method and apparatus for selectively increasing the cerebral temperature of a human while leaving the temperature of the rest of the body as is. The elevated temperature is selected from a narrow temperature range, and the rate of temperature change is limited.

GENERAL DESCRIPTION

The relationship between man's diurnal cycle or circadian rhythm and man's functioning on a variety of psychological tasks has been well established. Since the pioneering work of H. Marsh in 1906, research results have repeatedly demonstrated a consistent correlation between a subject's cerebral core temperature and such psychological or physiological functions as personality factors, mental efficiency, anxiety state, task rate, time estimation and production, visual acuity, flicker fusion rate, central arousal, autonomic response rate, and sensitivity to sensory stimuli. The majority of research studies support the conclusion that both the speed and accuracy of man's behavior is a function of his cerebral core temperature. The time response has been shown to covary inversely with rises in temperature, while accuracy has been shown to vary directly.

This invention produces direct behavioral change by selectively incrementing the temperature of the cortical surface in a person. This is in contrast to most research, which has focused upon the determination of behavioral changes as a result of the daily temperature fluctuations without directly attempting to manipulate cerebral temperature. Using a head-mounted, controlled heat source, evidence has been gathered to show that human brain temperature can be selectively incremented. Cortical temperatures have been monitored by the technique of tympanic thermography which is considered superior to either rectal or esophogeal calibration due to the proximity of the tympanic membrane to the hypothalamic regulatory area as well as the cortical surface. Although subjects were tested during the peak period of the normal diurnal cycle, regular and reliable temperature increments have been obtained. Moreover, this externally induced change appears unprecedented in the current literature as it involves neither an artificial alteration of the circadian rhythm nor the prior activation of the endrocrine system.

Using measures of both speed and accuracy in a pilot program of research to determine the behavioral consequences of such induced brain temperature changes, three studies of the invention have shown a significant trend (across all subjects) toward faster processing of sensory information and reduced decision time as a function of the thermal increments.

The first study investigated performance in a simple affirmative reaction time (RT) task under conditions of thermal treatment, a no-treatment control, and a pseudo-treatment placebo (apparatus mounted and monitored, but no thermal increments). Whereas the control and placebo results were found to be virtually overlapping, the RT for the treatment condition was significantly faster overall. FIG. IA, (Experiment I) shows that the mean median RT for the thermal treatment group produced shortened RT compared to either the control or the placebo conditions (median test, $X^2=4.61$, $df=2$, $p<0.10$). Comparison of treatment and placebo groups (controlling for subjective expectancy as subjects were unable to differentiate between the presence or absence of applied heat given the slow rise time) showed a significant RT difference in favor of the thermal group (direct difference $t$ test, $t=1.46$, $df=11$, $p<0.10$, one-tailed). In this and the following two studies, order effects have been counterbalanced through the use of a latin-square procedure.

The second study examined performance as a function of temperature change in a modification of the RT paradigm. In order to alter the decision making difficulty of the task without affecting the motoric component, a compatibility study was run in which subjects were given a unique rule for the correct response configuration i.e. "add one to the right", or an "alternation pattern". Although subjects under conditions of thermal increment or no change showed a decrease in RT across trials, subjects' RT in the thermal conditions was significantly less variable at asymptote (test for homogeneity of variance, $F (9,9) = 3.76$, $p<0.05$). This effect is shown in FIG. IB (Experiment II).

The third study assessed the effect of cortical temperature change upon visual scan rate. Using the paradigm outlined by U. Neisser (Scientific American 1964, Vol. 210, pp. 94–102), subjects were instructed to scan a column of five letter lines searching for the one line containing the designated target letter. By varying the line position (as well as the serial position within the line), the resultant RT functions were fitted by a linear regression equation to determine the unit time per item scanned. This estimate was derived from the slope of the regression equation in the same manner used by Neisser and by others. Again, as FIG. IC shows, comparisons between subject conditions of either ambient temperature or cortical increment produced scan rate estimates favoring a significantly faster, thereby more efficient, rate under conditions of increased brain temperature ($t = 1.40$, $df=7$, $p<0.10$, one tailed).

These pilot studies, conducted during the period of normal diurnal core temperature maxima of the subjects, indicate that a change in relative brain temperature reliably increments the speed of processing sensory information, decision making, and response initiation. Although the measured temperature changes have been small ($<2°$ F), the effect has proven to be replicable.

The invention thus provides equipment and procedures for imposing a selected elevated body-differential cerebral temperature on a person, within a selected temperature range and with a maximum rate of temperature change.

As used herein, the term "body-differential", as in the phrase "body-differential cerebral temperature", designates a body temperature that is localized to the cerebral area, i.e. the brain or entire head, and does not extend to other parts of the body and specifically excludes portions below the neck.

An object of the invention is to provide an improved method and apparatus for enhancing human cerebral functions, particularly without surgery or use of chemicals. Typical enhanced cerebral functions which the invention seeks to provide are an increased speed of response, and improved pattern recognition. A further enhancement is to reduce the variability between subjects; this, for example has important applications among operators of complex equipments and for communication between people engaged in a demanding task, such as between aircraft traffic controllers and between pilots. The method and apparatus of the invention accordingly can be used with people of normal mentality and mental ability, as well as by people with a cerebral abnormality or with special behavior.

The invention accordingly comprises the several steps and the relation of one or more of such steps in respect to each of the others, and the apparatus embodying features of construction, combination of elements and arrangements of parts adapted to affect such steps, all as exemplified in the following detailed disclosure, and the scope of the invention is indicated in the claims when read in conjunction with this disclosure.

DESCRIPTION OF DRAWINGS

For a fuller understanding of the nature and objects of the invention, reference should be made to the following detailed description and the accompanying drawings, in which.

DESCRIPTION OF ILLUSTRATED EMBODIMENTS

Figure 2:
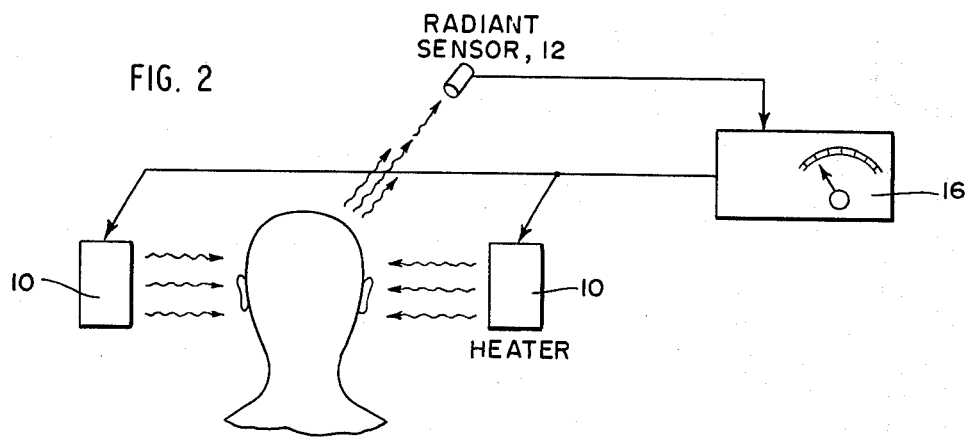
FIG. 2 is a schematic illustration of the invention.

FIG. 2 shows that the invention in its general terms provides a heater 10 for providing a selected controlled elevation of the temperature of a person's head. It is note-worthy that the heater applies a body-differential temperature to the head only, it does not effect any portion of the person's body other than the head. Hence, the rest of the body is at a natural body temperature according to the environmental conditions, clothing and the like.

A sensor 12 produces an electrical signal responsive to the person's head temperature. A control unit 14 receives the temperature-responsive sensor signal and operates the heater 10 in response to the difference between the sensed temperature as reported by sensor 12 and the setting of the unit, which typically is by a manual control 16. The control unit can be set, e.g. with the control 16, to maintain the person's head at a temperature selected from within the range of 38° to 50° C. Moreover, the control unit will operate the heater 10 to attain and maintain this selected value of head temperature with a limited rate of temperature increase. Further, it is preferable that upon termination of the period during which the person has been subjected to the elevated temperature from the heater 10, and the control unit is set (either manually or automatically) to return the head temperature to normal, e.g. 37° C, the control unit maintains the rate of temperature decrease below a selected rate.

As discussed hereinabove, it has been found that when the head temperature is maintained at an elevated level, thereby raising the cortical temperature of the person, the person's cerebral performance is enhanced. The actual temperature selected from within the specified range depends on factors such as the task, the performance to be achieved, the duration of the task, and the person or class of persons. The level appropriate for the given situation can be determined readily, typically after a few trials with different persons in the grouping.

The limited rates of temperature increase and temperature decrease noted above have been found to minimize or avoid discomfort during the transition between normal temperature and the selected elevated temperature. Moreover, temperature changes imposed at faster rates have been observed to produce, in some instance, cortical temperature instabilities. In view of these factors, a maximum rate of temperature increase below 1.0° C/min., and a maximum rate of decrease of about 0.5° C/min., are considered appropriate for practice of the invention. Preferred rates are below 0.8° C/min. for temperature increase and below 0.4° C/min. for temperature decrease.

Figure 3:
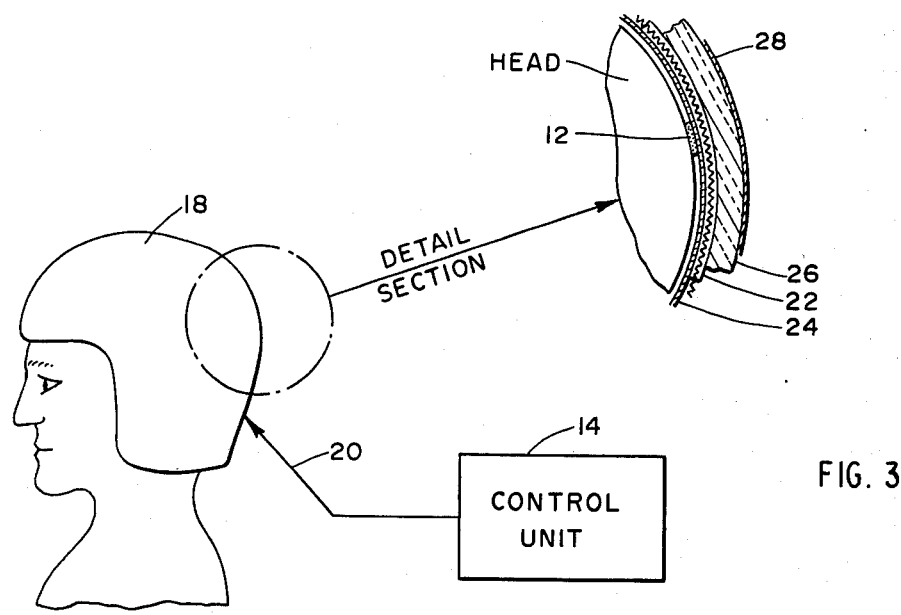
FIG. 3 shows a preferred construction for the heater of FIG. 2.

Turning to FIG. 3, the invention typically is practiced with the heater and sensor of FIG. 2 incorporated in a hood-like garment or helmet 18. The helmet preferably covers the exterior of the skull, including the frontal portion and the side and rear portions to below the ears.

As the detail of FIG. 3 shows, the helmet 18 preferably is constructed with an electrical resistance type heating element 22 adjacent the inner surface to be in close thermal contact with the wearer. An inner cover 24 generally is provided between the heating element and the head. It preferably has the properties of low thermal resistance, wearer comfort, and protection for the heating element 22 which it covers. Disposed over the heating element are a layer of thermal insulation 26 and a protective outer shell 28.

Although constructions of the heater 10 other than the illustrated helmet arrangement can be used, the principles embodied in FIG. 3 are considered preferable. These include coverage by the heating element over the skull frontal, top, back and side portions as shown; and relatively close thermal contact between the heating element and the wearer's head, but insulation of the heater from the environment.

Figure 4:
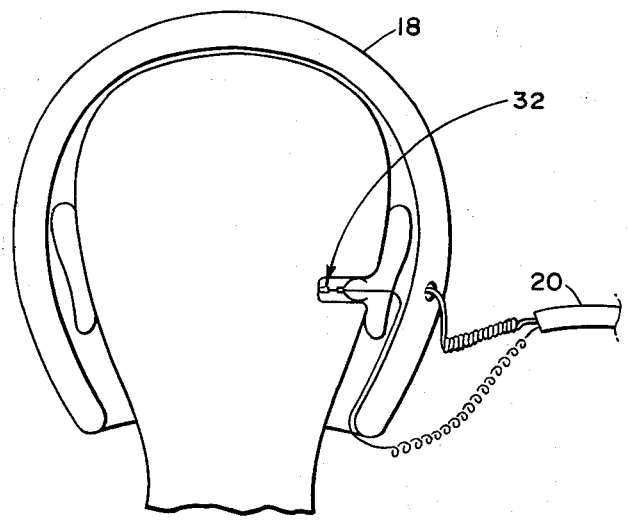
FIG. 4 illustrates the practice of the invention with a tympanic membrane sensor.

FIG. 3 also shows a thermistor disposed between the inner cover 24 and the heating element 22 to function as the sensor 14 of FIG. 2. The thermistor, which is illustrative of the other known temperature-responsive electrical elements that can provide the desired sensor function, is thus closely thermally coupled to the temperature which the heater imposes on the person's head. Moreover, with this arrangement, the sensor is an integral part of the helmet 18, and is automatically put in place. Also, a single multiple-conductor electrical cable 20 interconnects both the sensor and the heater with the control unit. Another arrangement for the sensor is to use a tympanic membrane construction, as FIG. 4 illustrates with the tympanic sensor 32. This sensor arrangement can be more precise than that shown in FIG. 3, but it requires insertion separate from the helmet and an electrical cable arrangement of the form illustrated in FIG. 4.

Figure 5:
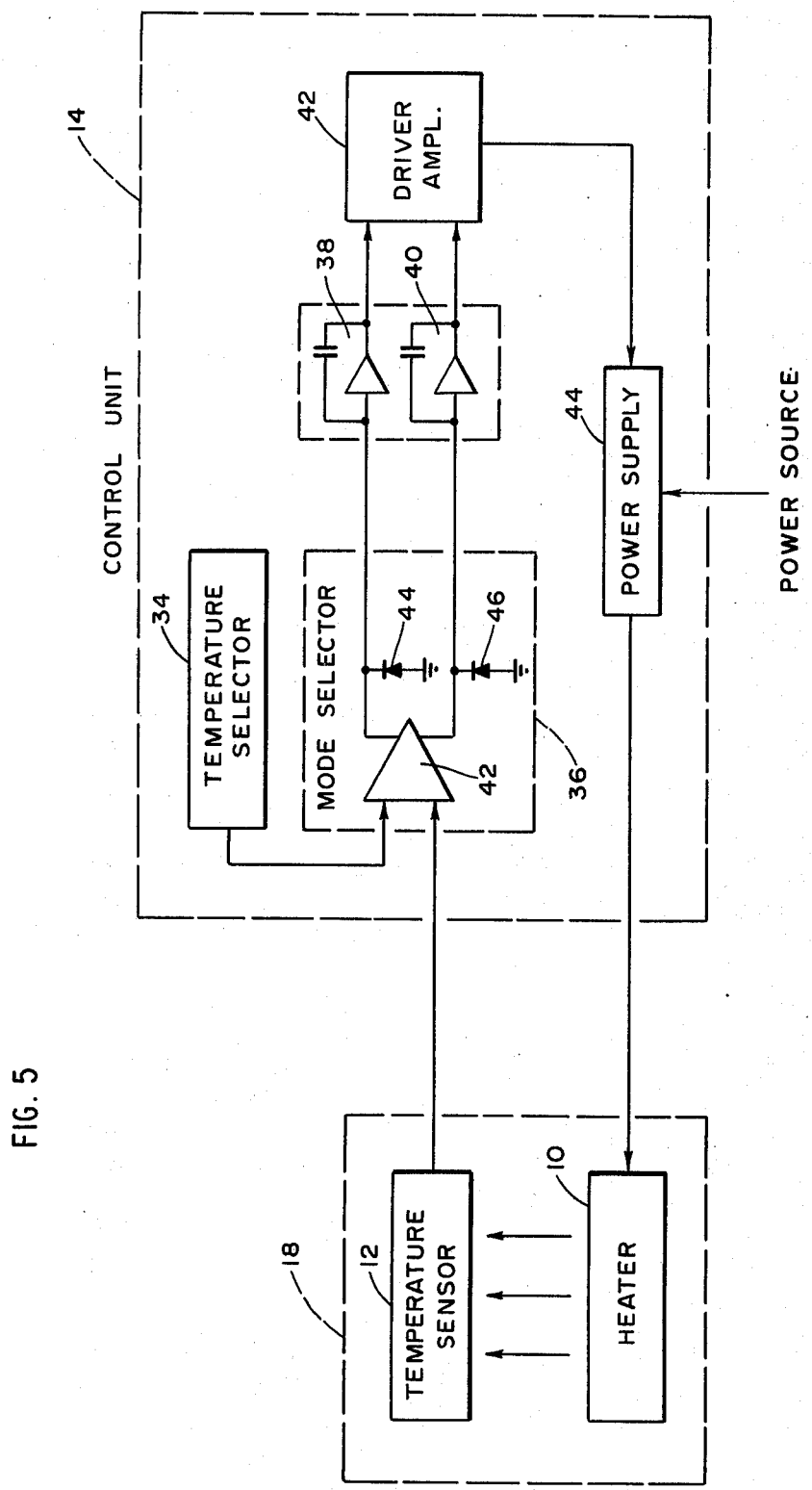
FIG. 5 is a block schematic diagram showing a control unit for practicing the invention.

Turning to FIG. 5, it illustrates a preferred arrangement of the control unit 14 for practicing the invention. The heater 10 and the temperature sensor 12 are illustrated incorporated in a uniting structure such as the helmet 18. As discussed above, the control unit 14 receives the temperature responsive signal from the sensor and in response drives the heater to apply the desired heat to the wearer. To provide this operation with a temperature selected from a specified range and with limited rates of temperature increase and of temperature decrease, the control unit has a temperature selector 34 connected to one input of a mode selector 36. The other input to the selector is the signal from the temperature sensor 12. By way of example, the temperature selector 50 can include a voltage divider that is manually set to the specified elevated temperature, or to ambient, by way of the manual control 16 of FIG. 2.

The mode selector functions to produce an error signal proportioned to the difference between the selector signal and the sensor signal it receives, and to apply the error signal to one of two integrators 38 and 40 depending on the relative polarity of the two signals. The mode selector accordingly can be constructed with a differential amplifier 42 having complementary outputs, each of which feeds a different integrator. Diodes 44 and 46 remove negative outputs, so that each integrator receives only a positive signal. The time constant of the integrator 38 limits the rate of temperature increase, and the integrator 40 has a time constant to limit the rate of temperature decrease, to the values specified above. Each integrator can be constructed to operate with a time constant that can be selectively adjusted within the specified limit.

A driver amplifier 42 receives the integrated signal from whichever integrator is operative, and in turn operates a power supply 44 to supply electrical exitation to the heater from a power source, which typically is a 60-cycle 110-volt supply.

The foregoing electrical system for practicing the invention is illustrative of those known in the art and which can be constructed using conventional skills well known to those practiced in this art.

It will thus be seen that the objects set forth above, among those made apparent from the preceding description, are efficiently attained. Since certain changes may be made in the above constructions and in carrying out the above techniques without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described the invention, what is claimed as new and secured by letters patent is:

1. Cortical temperature — elevating apparatus for imposing a selected elevated body-differential cortical temperature to a person, said apparatus comprising
   A. controllable thermal means for the localized heatinhg of the head of a person,
   B. sensor means for sensing the temperature of the person's head, and
   C. control means connected with said sensor means to receive a temperature-responsive signal and controlling in response thereto said thermal means to apply a temperature selected from the range between 38° and 50° C to the person's head, with a maximum rate of temperature increase below 1.0° C per minute.

2. Apparatus according to claim 1 incuding a head garment mounting said thermal means for relatively high heat transfer with a wearer's head.

3. Apparatus according to claim 2 in which said sensor means includes a temperature sensor mounted with said garment for disposition in relatively close thermal contact with the wearer's head.

4. Apparatus according to claim 2 in which said sensor means includes a tympanic membrane temperature sensor.

5. Apparatus according to claim 1 further characterized in that said control means includes means for controlling said thermal means to regulate the rate of temperature decrease from said selected elevated temperature to the person's present normal level at a maximum rate below 0.5° C per minute.

6. Apparatus according to claim 1 further characterized in that said control unit includes means for limiting the rate of temperature increase to 0.8° C per minute.

7. Apparatus according to claim 6 further characterized in that said control unit includes means for limiting the rate of temperature decrease from an elevated level to normal, to 0.4° C per minute.

8. A method for enhancing human cerebral functioning comprising the steps of
   A. selectively elevating the cortical temperature by imposing a selected elevated body-differential temperature to the person's head,
   B. monitoring the head temperature during at least the interval of said temperature-elevation, and
   C. controlling the elevation of the head temperature in response to said monitoring to a temperature selected from the range between 38° C and 50° C, and controlling the rate of temperature increase to be less than 0.8° C per minute.

9. A method as defined in claim 8 in which said controlling step further includes the step of controlling the rate of temperature decrease from said selected temperature to the person's present normal level to a maximum rate of 0.4° C per minute.

* * * * *

UNITED STATES PATENT AND TRADEMARK OFFICE
CERTIFICATE OF CORRECTION

PATENT NO. : 4,002,175
DATED : January 11, 1977
INVENTOR(S) : David M. Brainard and Edward C. Brainard II It is certified that error appears in the above-identified patent and that said Letters Patent are hereby corrected as shown below:

Column 1, line 52, change "endrocrine" to --endocrine--.

Figure 1C:
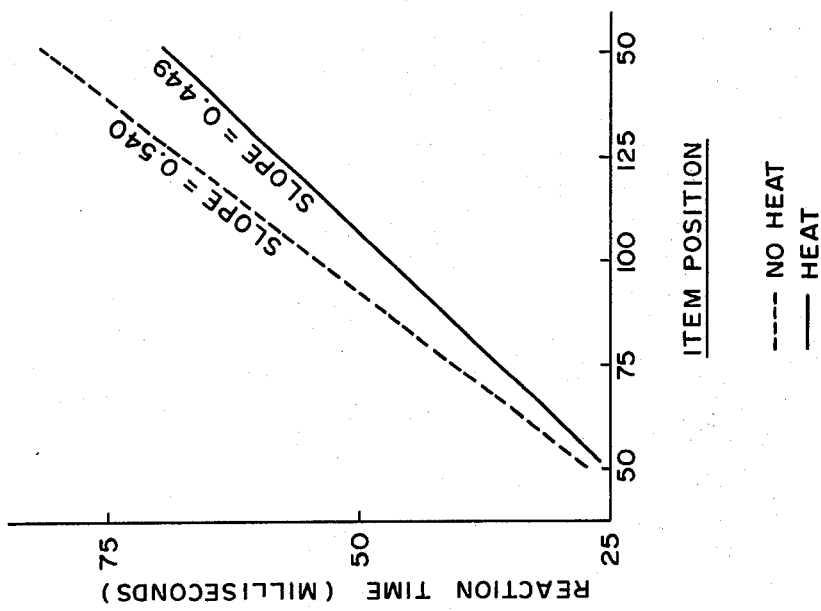
FIGS. 1A, 1B and 1C are graphs showing results obtained by initial practice of the invention.
Figure 1B:
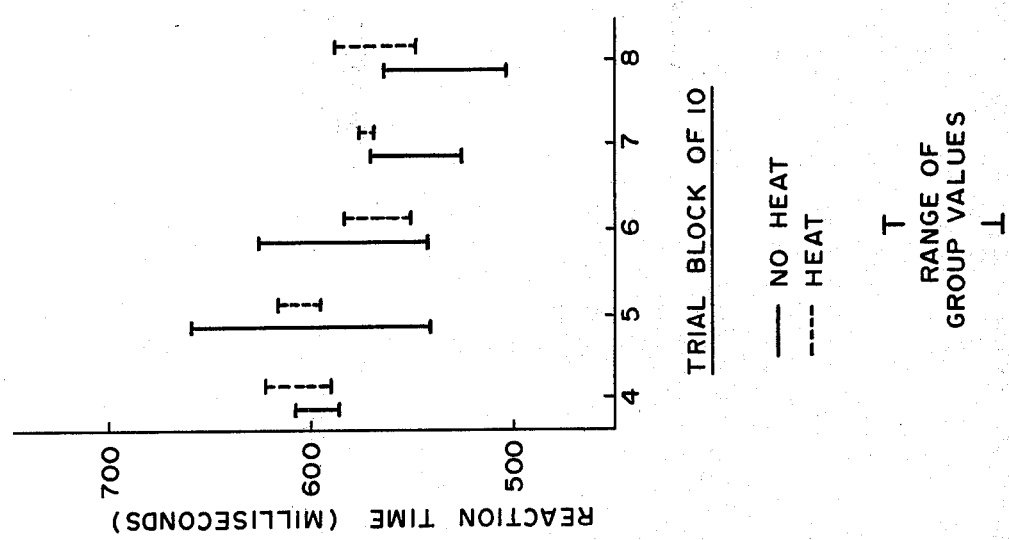
Figure 1A:
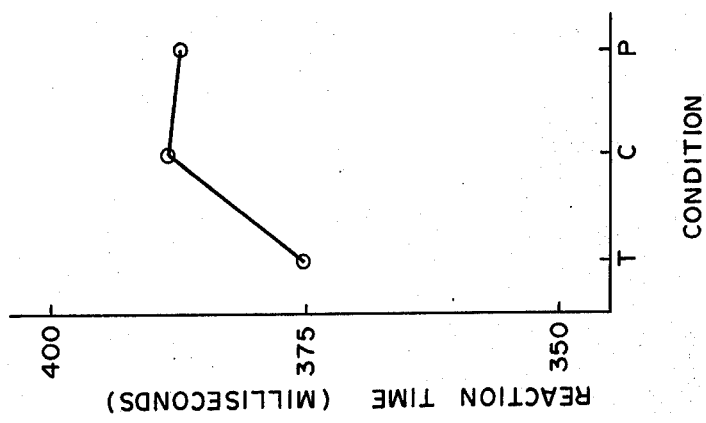

Column 1, line 68, "FIG. IA" should be --FIG. 1A--.

Column 2, line 25, "FIG.IB" should be --FIG. 1B--.

Column 2, line 37, "FIG. IC" should be --FIG. 1C--.

Column 6, line 5, change "tinhg" to --ting--.

Column 6, line 15, change "incuding" to --including--.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks